US005861394A

United States Patent [19]
Urbahns et al.

[11] Patent Number: 5,861,394
[45] Date of Patent: Jan. 19, 1999

[54] USE OF N-SUBSTITUTED PHENOTHIAZINES

[75] Inventors: Klaus Urbahns, Wuppertal; Hans-Georg Heine, Krefeld; Bodo Junge; Rudolf Schohe-Loop, both of Wuppertal; Henning Sommermeyer, Köln; Thomas Glaser, Overath; Reilinde Wittka, Köln; Jean-Marie-Viktor de vry, Rösrath, all of Germany

[73] Assignee: Bayer Aktiengesellschaft, Leverkusen, Germany

[21] Appl. No.: 793,619

[22] PCT Filed: Aug. 14, 1995

[86] PCT No.: PCT/EP95/03212

§ 371 Date: Feb. 19, 1997

§ 102(e) Date: Feb. 19, 1997

[87] PCT Pub. No.: WO96/05837

PCT Pub. Date: Feb. 29, 1996

[30] Foreign Application Priority Data

Aug. 25, 1994 [DE] Germany ............ 44 30 091.3

[51] Int. Cl.⁶ .............. A61K 31/54; C07D 279/30; C07D 279/28; C07D 279/26
[52] U.S. Cl. ............... 514/225.2; 514/225.5; 514/226.2; 540/599; 544/38; 544/39; 544/41
[58] Field of Search ............ 544/39, 38, 41; 540/599; 514/225.2, 226.2, 225.5

[56] References Cited

U.S. PATENT DOCUMENTS

| 4,666,907 | 5/1987 | Fortin | 544/39 |
| 4,833,138 | 5/1989 | Olney | 514/226.2 |
| 5,502,049 | 3/1996 | Garret | 514/225.2 |

FOREIGN PATENT DOCUMENTS

| M-7430 | 7/1970 | France . |
| 56-166183 | 12/1981 | Japan . |

OTHER PUBLICATIONS

Eur. J. Med Chem–Chem Ther. 12(5) 488 (1977).
Pharmazie, 26(6) 341–7 (1971).
Spasova, Chem Abs 81, 91455 p. (1974).
Brufani, II Farmaco 47, 585–597, 1992.
Strosznajder, Abstract for FEBS Letters 257, 110–112, Oct. 1989.
Strosznajder, Abstract for Neuroscience Lettes 114, 329–332, Jul. 1989.
Umemura, Abstract for J. Neurosurgery 76, 648–651, Apr. 1992.
Hattori, Abstract for Neurological Research 9, 164–8, Sep. 1987.
Ebstein, Abstract for Psychiatry Research 24, 45–52, Apr. 1988.
P.W.L. Tas, et al., Neurosci. Lett., vol. 94, pp. 279–284 (1988).
Japanese Patent Abstracts, Abstract of JP56–166, 183 (1981).
R.C. Kelsey, et al., Arch. Int. Pharmacodyn. Ther., vol. 173, No. 1, pp. 44–56 (1968).

*Primary Examiner*—Mark L. Berch
*Attorney, Agent, or Firm*—Sprung Kramer Schaefer & Briscoe

[57] ABSTRACT

The invention relates to the use of N-substituted phenothiazines for the production of medicaments for the treatment of cerebral disorders. The invention likewise relates to novel active compounds which are prepared by reaction of phenothiazine with the appropriate acids, esters or amides or by reaction of the phenothiazinecarbonyl halides with amines. The active compounds are particularly suitable for the treatment of dementias and age-related leaning and memory disorders and depressions.

6 Claims, No Drawings

USE OF N-SUBSTITUTED PHENOTHIAZINES

The present invention relates to the use of N-substituted phenothiazines for the production of medicaments, to novel active compounds and to a process for their preparation, in particular to use as cerebrally active agents.

It is already known that 10-carboxamido-substituted phenothiazines have an antitumour action [cf JP 561 66 183 A2, 1981]. The publication U.S. Pat. No. 4,833,138 additionally describes phenothiazine derivatives for the treatment of neurotoxic disorders. Effects of some phenothiazines in the intrapleural fluid test are furthermore mentioned in the publication Arch Int. Pharmacodyn. Ther. 173 (1), 44–55, (1968).

It has now been found that N-substituted phenothiazines of the general formula (I)

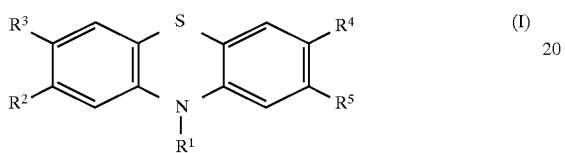

in which
$R^1$ represents a radical of the formula —$(CH_2)_a$—CO—$R^6$, —$(CH_2)_a$—CO—$NR^7R^8$ or —$(CH_2)_b$—$R^9$,
wherein
a denotes a number 0, 1 or 2,
b denotes a number 1 or 2,
$R^6$ denotes hydrogen or straight-chain or branched alkoxy or alkyl in each case having up to 6 carbon atoms, it being possible for the latter to be substituted by halogen or hydroxyl,
$R^7$ denotes hydrogen or straight-chain or branched alkyl having up to 6 carbon atoms, which is optionally substituted by halogen,
$R^8$ denotes hydrogen, cycloalkyl having 3 to 6 carbon atoms, pyridyl, phenyl, amino or straight-chain or branched alkyl having up to 6 carbon atoms, which is optionally substituted by hydroxyl or pyridyl,
or
$R^7$ and $R^8$, together with the nitrogen atom, form a piperidine, morpholine, azacycloheptyl or pyrrolidinyl ring,
$R^9$ denotes cyano or straight-chain or branched alkoxycarbonyl having up to 6 carbon atoms,
$R^2$, $R^3$, $R^4$ and $R^5$ are identical or different and represent hydrogen, halogen or trifluoromethyl,
and their salts surprisingly have a modulating action on potassium channels and are thus suitable for use in the control of disorders of the CNS and sickle cell anemia.

In the context of the invention physiologically acceptable salts are preferred.

Physiologically acceptable salts are in general salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid or methanesulphonic acid, etanesulphonic acid, phenylsulphonic acid, toluenesulphonic acid or naphthalenedisulphonic acid.

The compounds according to the invention can exist in stereoisomeric forms which either behave as image and mirror image (enantiomers), or which do not behave as image and mirror image (diastereomers). The invention relates both to the antipodes and to the racemic forms as well as the diastereomer mixtures. Like the diastereomers, the racemic forms can also be separated into the stereoisomerically uniform constituents in a known manner.

Preferred are those compounds of the general formula (I) in which
$R^1$ represents a radical of the formula —$(CH_2)_a$—CO—$R^6$, —$(CH_2)_a$—CO—$NR^7R^8$ or —$(CH_2)_b$—$R^9$,
wherein
a denotes a number 0, 1 or 2,
b denotes a number 1 or 2,
$R^6$ denotes hydrogen or straight-chain or branched alkoxy or alkyl in each case having up to 4 carbon atoms, it being possible for the latter to be substituted by fluorine, chlorine or hydroxyl,
$R^7$ denotes hydrogen or straight-chain or branched allyl having up to 4 carbon atoms, which is optionally substituted by chlorine,
$R^8$ denotes hydrogen, pyridyl, phenyl, amino, cyclopropyl, cyclopentyl, cyclohexyl or straight-chain or branched alkyl having up to 4 carbon atoms, which is optionally substituted by hydroxyl or pyridyl,
or
$R^7$ and $R^8$, together with the nitrogen atom, form a piperidine, morpholine, azacycloheptyl or pyrrolidinyl ring,
$R^9$ denotes cyano or straight-chain or branched alkoxycarbonyl having up to 4 carbon atoms,
$R^2$ and $R^5$ are identical or different and represent hydrogen, fluorine, chlorine, bromine or trifluoromethyl,
$R^3$ and $R^4$ represent hydrogen,
and their salts,
in the control of disorders of the CNS.

Particularly preferred are those compounds of the general formula (I)
in which
$R^1$ represents a radical of the formula —$(CH_2)_a$—CO—$R^6$, —$(CH_2)_a$—CO—$NR^7R^8$ or —$(CH_2)_b$—$R^9$,
wherein
a denotes a number 0, 1 or 2,
b denotes a number 1 or 2,
$R^6$ denotes hydrogen or straight-chain or branched alkoxy or alkyl in each case having up to 4 carbon atoms, it being possible for the latter to be substituted by fluorine, chlorine or hydroxyl,
$R^7$ denotes hydrogen or straight-chain or branched alkyl having up to 4 carbon atoms, which is optionally substituted by chlorine,
$R^8$ denotes hydrogen, pyridyl, phenyl, amino, cyclopropyl, cyclopentyl, cyclohexyl or straight-chain or branched alkyl having up to 4 carbon atoms, which is optionally substituted by hydroxyl or pyridyl,
or
$R^7$ and $R^8$, together with the nitrogen atom, form a piperidine, morpholine, azacycloheptyl or pyrrolidinyl ring,
$R^9$ denotes cyano or straight-chain or branched alkoxycarbonyl having up to 4 carbon atoms,
$R^2$ and $R^5$ are identical or different and represent hydrogen, fluorine, chlorine, bromine or trifluoromethyl,
$R^3$ and $R^4$ represent hydrogen,
and their salts,
in the control of disorders of the CNS.

The compounds of the general formula (I) according to the invention show an unforeseeable, useful spectrum of pharmacological action.

They are channel modulators having selectivity for calcium-dependent potassium channels of high conductivity (BK(Ca) channels), in particular of the central nervous system.

On account of their pharmacological properties, they can be employed for the production of medicaments for the treatment of degenerative central nervous system disorders, such as, for example, on occurrence of dementias such as multiinfarct dementia (MID), primary degenerative dementia (PDD), presenile and senile dementia of the Alzheimer's disease type, HIV dementia and other forms of dementia. They are furthermore suitable for the treatment of Parkinson's disease or amyotrophic lateral sclerosis and also multiple sclerosis.

The active compounds are furthermore suitable for the treatment of brain function disorders in old age, of organic brain syndrome (OBS) and of age-related memory disorders (age-associated memory impairment, AAMI).

They are suitable for the prophylaxis, for the treatment and for the control of the sequelae of cerebral circulatory disorders such as cerebral ischaemias, strokes, cerebrocranial traumata and of subarachnoid hemorrhages.

They are useful for the treatment of depressions and psychoses, e.g. schizophrenia. They are additionally suitable for the treatment of disorders of neuroendocrine secretion and of neurotransmitter secretion and health disorders connected therewith such as mania, alcoholism, drug abuse, dependence or abnormal eating behaviour. Further application areas are the treatment of migraine, sleep disorders and of neuropathies. They are moreover suitable as analgesics.

The active compounds are furthermore suitable for the treatment of disorders of the immune system, in particular of T-lymphocyte proliferation and for affecting the smooth musculature, in particular of uterus, urinary bladder and bronchial tract and for the treatment of diseases connected therewith, such as e.g. asthma and urinary incontinence, and for the treatment of high blood pressure, arrhythmia, angina and diabetes.

The invention additionally relates to new compounds of the general formula (Ia)

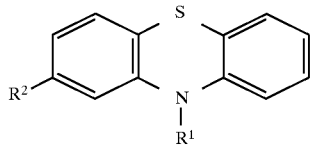
(Ia)

and their salts
having the substituent meanings indicated in the following table:

| $R^1$ | $R^2$ |
|---|---|
| —CO—NH—(pyridyl) | H |
| —CO—N(CH$_3$)—C$_6$H$_5$ | H |
| —CO—(CH$_2$)$_3$—Cl | Cl |
| —CO—(CH$_2$)$_3$—Cl | H |
| —CO—N((CH$_2$)$_3$CH$_3$)$_2$ | H |
| —CO—N(CH$_3$)—C$_6$H$_{11}$ | H |
| —(CH$_2$)$_2$—CO—NH—C$_2$H$_5$ | Cl |
| —(CH$_2$)$_2$—CO—NH(CH$_2$)$_3$—CH$_3$ | Cl |
| —(CH$_2$)$_2$—CO—NH—(CH$_2$)$_3$—CH$_3$ | H |
| —(CH$_2$)$_2$—CO—NH—CH$_2$—(pyridyl) | Cl |
| —(CH$_2$)$_2$—CO—NH—(CH$_2$)$_2$CH$_3$ | H |
| —(CH$_2$)—CO—N(CH$_2$CH$_3$)$_2$ | H |
| —CO—N(pyrrolidinyl) | H |
| —CO—N(morpholinyl) | H |
| —CO—N(azepanyl) | H |
| —CH$_2$—CO—NH—(CH$_2$)$_3$CH$_3$ | H |
| —CH$_2$—CO—NH—(CH$_2$)$_2$CH$_3$ | H |
| —CH$_2$—CO—NH—C$_2$H$_5$ | H |
| —CH$_2$—CO—NH((CH$_2$)$_2$CH$_3$)$_2$ | H |

The compounds of the general formula (I) according to the invention are prepared by either directly reacting phenothiazine with the appropriate acids, esters or amides of the general formula (I)

$$E—R^1 \qquad (II)$$

in which
E represents a typical leaving group, such as, for example, chlorine or iodine, preferably chlorine,
in inert solvents and in the presence of a base, if appropriate under a protective gas atmosphere
or
in the case of the amides —(CH$_2$)$_a$—CO—NR$^7$R$^8$, starting from the appropriate acid chlorides of the general formula (Ib)

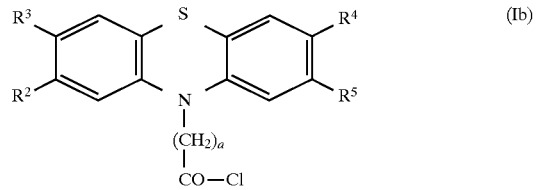
(Ib)

in which
$R^2$ to $R^5$ and a have the meaning indicated,
reacting with amines of the general formula (III)

$$H—NR^7R^8 \qquad (III)$$

in which
$R^7$ and $R^8$ have the scope of meaning indicated,
in inert solvents, if appropriate in the presence of a firer base and if appropriate under a protective gas atmosphere.

The process according to the invention can be illustrated by way of example by the following reaction scheme:

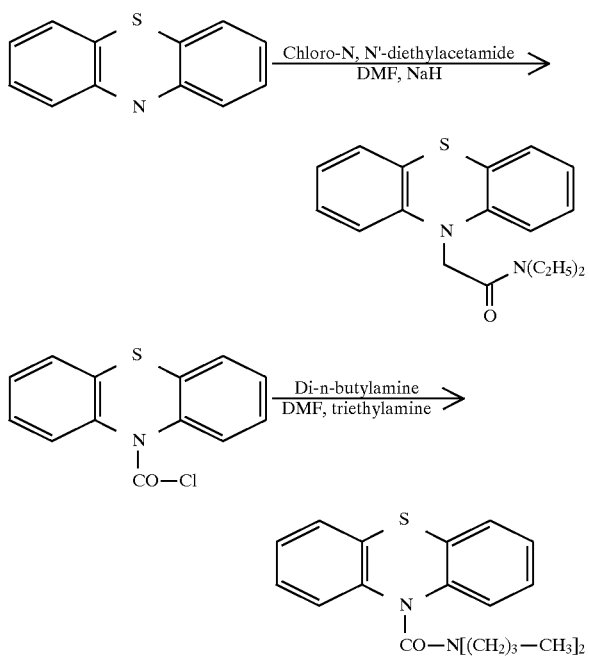

Suitable solvents in this case are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether or diethylene glycol dimethyl ether, acetonitrile, or amides such as hexamethylphosphoramide or dimethylformamide, or halogenated hydrocarbons such as methylene chloride or carbon tetrarhloride, or hydrocarbons such as benzene or toluene. It is also possible to use mixtures of the solvents mentioned. Dimethylformamide is particularly preferred Suitable bases are in general alkali metal hydrides or alkoxides, such as, for example, sodium hydride or potassium tert-butoxide, or cyclic amines, such as, for example, piperidine, dimethylaminopyridine or $C_1$–$C_4$-alkylamines, such as, for example, triethylamine. Depending on the particular reaction steps, triethylamine and sodium hydride are preferred.

When carrying out the process according to the invention, any desired ratio of the substances participating in the reaction can be used. In general, however, the reaction is carried out with molar amounts of the reactants.

The reaction temperatures can be varied within a relatively wide range. In general the reaction is carried out at between –10° C. and +150° C., preferably between 0° C. and +100° C., in particular at the boiling point of the respective solvent The reactions can be carried out at normal pressure, but also at elevated or reduced pressure (e.g. 0.5 to 3 bar). In general the reactions are carried out at normal pressure.

For some reaction steps reaction under a protective gas atmosphere is appropriate.

To activate the carboxylic acid, suitable reagents are the customary reagents such as inorganic halides, for example thionyl chloride, phosphorus trichloride or phosphorus pentachloride, or carbonyldiimidazole, carbodiimides such as cyclohexylcarbodiimide or 1-cyclohexyl-3-[2-N-methyhorpholino)ethyl]-carbodiimide p-toluenesulphonate or N-hydroxyphthalimide or N-hydroxy-benzotriazole.

The enantiomerically pure compounds are also accessible by chromatography of the racemic esters on chiral phases.

The compounds of the general formulae (II) and (III) are known.

The phenothiazine-10-carbonyl chlorides of the general formula (Ia) are known in some cases or are new and can then be prepared, for example, as described above by reaction of phenothiazine with the appropriate acid chlorides.

Nomenclature name N,N di-n-propylphenothiazine-10-carboxamide (U.S. Pat. No. 4,833,138); nomenclature name methyl 3-(phenothiazin-10-yl)propionate (WO 9 412 621; WO 9 412 619) and nomenclature name methyl 3-2chlorophenothiazin-10-yl) propionate (U.S. Pat. No. 2,820,031 (1953)) are known.

[86]Rubidium efflux from C6-BU1 glioma cells

The experiments were carried out with slight modifications according to the method described by Tas et al. (Neurosci. Lett. 94, 279–284, (1988)). To do this, rat C6BU1 glioma cells are used.

From the data obtained by liquid scintillation, the increase in Rb efflux caused by ionomycin above the basal efflux is calculated and set as 100 %. The stimulations in the presence of test substances are then related to this value.

The present invention also includes pharmaceutical preparations which, in addition to inert non-toxic, pharmaceutically suitable auxiliaries and excipients, contain one or more compounds of the general formulae (I)/(Ia)/(Ib), or which consist of one or more active compounds, and processes for the production of these preparations.

The active compounds should be present in these preparations in a concentration from 0.1 to 99.5 % by weight, preferably from 0.5 to 95 % by weight of the total mixture.

In addition to the active compounds, the pharmaceutical preparations can also contain other pharmaceutical active compounds.

The abovementioned pharmaceutical preparations can be prepared in a customary manner by known methods, for example using the auxiliary(ies) or excipient(s).

In general it has proven expedient to administer the active compound(s) in total amounts from about 0.01 to about 100 mg/kg, preferably in total amounts from about 1 mg/kg to 50 mg/g of body weight every 24 hours, if appropriate in the form of several individual doses, to achieve the desired result.

However, if appropriate it may be advantageous to depart from the amounts mentioned, namely depending on the nature and the body weight of the subject tread, on individual behaviour towards the medicament, the nature and severity of the disorder, the type of preparation and administration, and the time or interval at which administration takes place.

Key for the TLC Mobile Phase Mixtures:

a) : ammonia/MeOH/$CHCl_3$/AcOEt/n-hexane 1:10:100:1.7:3
b) : toluene/AcOEt 10:1
c) : toluene/AcOEt 3:1
d) : toluene/AcOEt 1:1

PREPARATION EXAMPLES

Example 1

(Phenothiazin-10-yl)-N,N-diethylacetamide

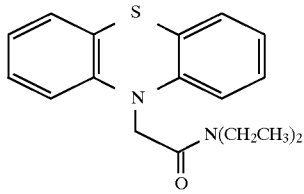

29.9g (150 mmol) of phenothiazine are treated in portions at 25° C. in 400 ml of dimethylformamide under nitrogen with a total of 3.9 g (160 mmol) of sodium hydride. After stirring for 30 min, 25.0 g (160 mmol) of 2-chloro-N,N'-ethylacetamide (97%) in 50 ml of dimethylformamide are added dropwise in the course of 30 minutes. After stirring overnight at 25° C., the mixture is added to ice and extracted with dichloromethane. The organic phase is washed twice with sodium chloride solution, dried over anhydrous sodium sulphate and concentrated in vacuo. The residue is chromatographed on 1000 g of silica gel using toluene/ethyl acetate (gradient) and yields 18.8 g of colourless crystals. M.p. 129°–130° C. (from dichloromethane/diethyl ether).

Example 2

Phenothiazine-10-N,N-di-n-butylcarboxamide

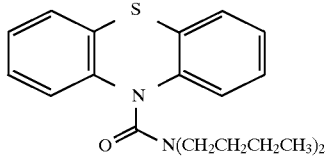

5.3 g (20 mmol) of phenothiazine-10-carbonyl chloride are treated successively at 0° C. in 80 ml of dichloromethane with 2.6 g (20 mmol) of di-n-butylamine and 2.8 g (20 mmol) of triethylamine and the mixture is stirred at 25° C. for 72 h. The reaction solution is treated with 1N hydrochloric acid, then washed with water, dried over anhydrous sodium sulphate and evaporated in vacuo. The residue is chromatographed on silica gel (flash chromatography) and affords 4.5 g (63%) of colourless crystals. Mp. 42°–43° C. (from petroleum ether, b.p. 40° C.).

Example 3

3-(Phenothiazin-10-yl)-N-n-butylpropionamide

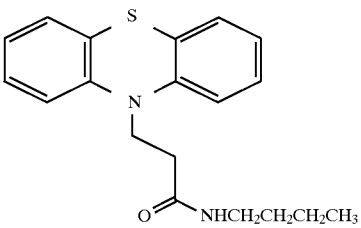

4.2 g (150 mmol) of methyl 3-(phenothiazin-10-yl)-propionate and 2.2 g (30 mmol) of n-butylamine are heated at 100° C. under nitrogen for 18 h. The reaction product taken up in 60 ml of methylene chloride is washed with 1N hydrochloric acid and then with water, dried over anhydrous sodium sulphate and concentrated in vacuo. The residue (4.9 g) is filtered through silica gel (flash chromatography). 4.8 g (98% of theory) of colourless crystals are obtained. Mp. 106°–107° C. (from dichloromethane/petroleum ether).

Example 4

3-(2-Chloro-phenothiazin-10-yl)N-n-butyl propionamide

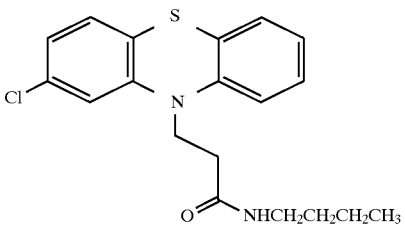

1.2 g (16 mmol) of n-butylamine and 1.6 g (2.2 ml, 16 mmol) of triethylamine are added successively with ice-cooling and stirring to 5.1 g (16 mmol) of 3-2-chloro-phenothiazin-10-yl)propionyl chloride in 100 ml of dichlorometane. After stirring at 25° C. for 20 h, the reaction solution is introduced into ice water and rendered alkaline with ammonia water (pH 9). Extraction with dichloromethane, washing of the dichlorometane extracts with water and subsequent drying over anhydrous sodium sulphate yield 5.3 g of crystalline product after evaporation in vacuo and chromatography of the residue on silica gel (100 g) using toluene/ethyl acetate. Crystallization from dichloromethane/petroleum ether affords 4.2 g (36% of theory) of the title compound. Mp. 89°–91° C.

The compounds listed in Tables 1, 2 and 3 are prepared in analogy to the abovementioned preparation procedures.

TABLE 1

[Structure: phenothiazine with R2' on one ring and R1' on N]

| Ex. No. | R2' | R1' | Yield (% of theory) M.p. (°C.) | $R_f$* |
|---|---|---|---|---|
| 5 | H | —CO—NH—(pyrid-4-yl) | 92/148–152 | 0.42/a |
| 6 | H | —CO—(CH$_2$)$_3$—Cl | 70/93–6 | 0.41/b |
| 7 | Cl | —CO—(CH$_2$)$_3$Cl | 62/109–12 | 0.59/b |
| 8 | Cl | —(CH$_2$)$_2$—CO—NH—CH$_2$—(pyrid-4-yl) | 42/128–9 | 0.49/g |
| 9 | H | —(CH$_2$)$_2$—CO—NH—(CH$_2$)$_2$—CH$_3$ | 73/131–3 | 0.67/b |
| 10 | Cl | —(CH$_2$)$_2$—CONH—(CH$_2$)$_2$CH$_3$ | 36/112–4 | 0.21/c |
| 11 | Cl | —(CH$_2$)$_2$—CO—NHC$_2$H$_5$ | 5/109–10 | 0.17/c |
| 12 | H | —CO—N(pyrrolidine) | 82/134–37 | 0.26/b |
| 13 | H | —CO—N(morpholine) | 74/133–37 | 0.38/c |
| 14 | H | —CO—N(azacycloheptyl) | 59/99–101 | 0.43/b |
| 15 | H | —CO—N(CH$_3$)—C$_6$H$_{11}$ | 80/169–71 | 0.38/b |
| 16 | H | —CO—N(CH$_3$)C$_6$H$_5$ | 49/126–29 | 0.35/b |
| 17 | H | —CH$_2$—CO—NH(CH$_2$)$_3$CH$_3$ | 60/153–54 | 0.32/d |
| 18 | H | —CH$_2$—CO—NH—(CH$_2$)$_2$CH$_3$ | 20/147–8 | 0.37/d |
| 19 | H | —CH$_2$—CO—NHC$_2$H$_5$ | 2/162–4 | 0.49/d |
| 20 | H | —CH$_2$—CO—N(CH$_2$CH$_2$CH$_3$)$_2$ | 51/91–3 | 0.55/d |

We claim:

1. N-substituted phenothiazines of the series
phenothiazine-10-N-(pyrid-4-yl)carboxamide
phenothiazine-10-N-methyl-N-phenylcarboxamide
phenothiazine-10-N-cyclohexyl-N-methylcarboxamide
3-(2-chloro-phenothiazin-10-yl)-N-ethylpropionamide
3-(2-chloro-phenothiazin- 10-yl)-N-propylpropionamide
3-(2-chloro-phenothiazin-10-yl)-N-(pyridin-4-ylmethyl)propionamide
3-(phenothiazine-10-yl)-N-propylpropionamide
phenothiazine-10-N,N-diethylacetamide
phenothiazine-10-carboxylic acid pyrrolidide
phenothiazine-10-carboxylic acid morpholide
phenothiazin-10-yl)-carboxylic acid azacycloheptylimide
(phenothiazin-10-yl)-N-n-propylacetamide
(phenothiazin-10-yl)-N-ethylacetamide
(phenothiazin-10-yl)-N,N-di-n-propylacetamide
phenothiazine-10-N-n-butylpropionamide
4-chloro-1-(2-chlorophenothiazin-10-yl)butan-1-one
4-chloro-1-(phenothiazin-10-yl)butan-1-one
phenothiazine-10-N-n-butylacetamide
3-(2-chlorophenothiazin- 10-yl)-N-n-butylpropionamide.

2. Process for the preparation of N-substituted phenothiazines according to claim 1, characterized in that
phenothiazine is reacted directly with the appropriate acids, esters or amides in inert solvents and in the presence of a base, if appropriate under a protective gas atmosphere
or the corresponding phenothiazine acid chlorides are reacted with amines in inert solvents, if appropriate in the presence of a filter base.

3. Medicaments containing at least one N-substituted phenothiazine according to claim 1 and customary formulation auxiliaries.

4. A method for treating cerebral ischemias, strokes, subarrachnoid hemorrhages, depression, psychosis or for treating sickle cell anemia which comprises administering to a host in need thereof an effective amount of a compound of the formula

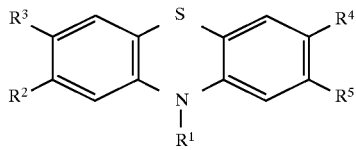

in which
R$^1$ represents a radical of the formula —(CH$_2$)$_a$—CO—R$^6$, —(CH$_2$)$_a$—CO—NR$^7$R$^8$ or —(CH$_2$)$_b$—R$^9$,
wherein
a denotes a number 0, 1 or 2,
b denotes a number 1 or 2,
R$^6$ denotes hydrogen or alkyl in each case having up to 6 carbon atoms, wherein said alkyl group is optionally substituted by halogen or hydroxyl,
R$^7$ denotes hydrogen or staight-chain or branched alkyl having up to 6 carbon atoms, which is optionally substituted by halogen,
R$^8$ denotes hydrogen, cycloalkyl having 3 to 6 carbon atoms, amino or straight-chain or branched alkyl having up to 6 carbon atoms, which is optionally substituted by hydroxyl or pyridyl,
or, when a denotes O.
R$^8$ denotes pyridyl or phenyl, or
R$^7$ and R$^8$, together with the nitrogen atom form a piperidine, morpholine, azacycloheptyl or pyrrolidinyl ring,
R$^9$ denotes cyano or straight-chain or branched alkoxycarbonyl having up to 6 carbon atoms,
R$^2$, R$^3$, R$^4$ and R$^5$ are identical or different and represent hydrogen, halogen or trifluoromethyl,
or a salt thereof.

5. The method according to claim 4 wherein
R$^1$ represents a radical of the formula —(CH$_2$)$_a$—CO—R$^6$, —(CH$_2$)$_a$—CO—NR$^7$R$^8$ or —(CH$_2$)$_b$—R$^9$,
wherein
a denotes a number 0, 1 or 2,
b denotes a number 1 or 2,
R$^6$ denotes hydrogen or alkyl in each case having up to 4 carbon atoms, wherein said alkyl group is optionally substituted by fluorine, chlorine or hydroxyl,
R$^7$ denotes hydrogen or straight-chain or branched alkyl having up to 4 carbon atoms, which is optionally substituted by chlorine,
R$^8$ denotes hydrogen, amino, cyclopropyl, cyclopentyl, cyclohexyl or straight-chain or branched alkyl having up to 4 carbon atoms, which is optionally substituted by hydroxyl or pyridyl,
or, when a denotes O,
R$^8$ denotes pyridyl or phenyl or
R$^7$ and R$^8$, together with the nitrogen atom, form a piperidine, morpholine, azacycloheptyl or pyrrolidinyl ring,
R$^9$ denotes cyano or straight-chain or branched alkoxycarbonyl having up to 4 carbon atoms,
R$^2$ and R$^5$ are identical or different and represent hydrogen, fluorine, chlorine, bromine or trifluoromethyl,
R$^3$ and R$^4$ represent hydrogen,
or a salt thereof.

6. The method according to claim 4 wherein
R$^1$ represents a radical of the formula —(CH$_2$)$_a$—CO—R$^6$, —(CH$_2$)$_a$—CO—NR$^7$R$^8$ or —(CH$_2$)$_b$—R$^9$,
wherein
a denotes a number 0, 1 or 2,
b denotes a number 1 or 2,
R$^6$ denotes hydrogen or alkyl in each case having up to 4 carbon atoms, wherein said alkyl group is optionally substituted by fluorine, chlorine or hydroxyl,
R$^7$ denotes hydrogen or straight-chain or branched alkyl having up to 4 carbon atoms, which is optionally substituted by chlorine,
R$^8$ denotes hydrogen, amino, cyclopropyl, cyclopentyl, cyclohexyl or straight-chain or branched alkyl having up to 4 carbon atoms, which is optionally substituted by hydroxyl or pyridyl,
or, when a denotes O,
R$^8$ denotes pyridyl or phenyl, or
R$^7$ and R$^8$, together with the nitrogen atom, form a piperidine, morpholine, azacycloheptyl or pyrrolidinyl ring,
R$^9$ denotes cyano or straight-chain or branched alkoxycarbonyl having up to 4 carbon atoms,
R$^2$ and R$^5$ are identical or different and represent hydrogen, fluorine, chlorine, bromine or trifluoromethyl,
R$^3$ and R$^4$ represent hydrogen,
or a salt thereof.

* * * * *